United States Patent [19]

Antypas

[11] 4,281,647
[45] Aug. 4, 1981

[54] INFLATABLE HAND SPLINT

[76] Inventor: Philip G. Antypas, 300 Lebanon Ave., Pittsburgh, Pa. 15228

[21] Appl. No.: 84,372

[22] Filed: Oct. 12, 1979

[51] Int. Cl.³ .............................................. A61F 5/10
[52] U.S. Cl. .............................. 128/77; 128/DIG. 20
[58] Field of Search .................... 128/77, 87 A, 87 R, 128/DIG. 20, 94

[56] References Cited

U.S. PATENT DOCUMENTS

| | | | |
|---|---|---|---|
| 3,771,519 | 11/1973 | Haake | 128/94 |
| 3,824,992 | 7/1974 | Nicholson et al. | 128/DIG. 20 |
| 4,173,218 | 11/1979 | Cronin | 128/77 |

Primary Examiner—John D. Yasko
Attorney, Agent, or Firm—Webb, Burden, Robinson & Webb

[57] ABSTRACT

An inflatable bandage splint for the hand comprising an inner glove of impermeable sheet material and an outer envelope of impermeable elastic sheet material. The inner glove and outer envelope are sealed together to form a fluid-tight chamber which may be inflated through a valve provided in the outer envelope. The inner glove and the outer envelope are secured together at selected distal locations and in the vicinity of the wrist. Eyelets are mounted to at least some of the distal locations where the inner glove and outer envelope are joined together. Eyelets are also provided in the vicinity of the wrist. Thus, when the bandage is inflated, tensile members such as elastic cord can be threaded through the eyelets and tied to pull the hand into the desired restrained position.

16 Claims, 6 Drawing Figures

INFLATABLE HAND SPLINT

BACKGROUND

This invention relates to the art of inflatable splints and bandages. Prior art patents directed to either zippered or wrapped-around inflatable splints and bandages include, for example, U.S. Pat. Nos. Re. 26,046; 1,884,927; 2,823,668; 3,548,819; 3,561,435; 3,762,404; 3,785,375 and 3,901,225. Currently are marketed bandage splints that define a double walled enclosure into which a limb may be inserted whereupon the space between the walls is inflated to immobilize the limb.

The applicant is a surgeon with extensive experience in hand surgery and is aware of a need for a unique inflatable bandage splint for immobilizing the hand after surgery. The prior art referenced above does not fulfill this need. It is a primary object according to this invention to provide an inflatable bandage splint which can be used to immobilize the fingers, hand and wrist and to supply compression as needed. Thus the inflatable bandage splint can be used as a splint to immobilize the fingers, hand and wrist or when lined with gauze or linen on the inside it can be used as a dressing to cover wounds. The inflatable bandage splint may be used to apply compression to the hand to reduce or prevent swelling. The degree of compression can be controlled by the pressure to which the bandage splint is inflated. This may be effected by use of the readily available blood pressure apparatus thus enabling one to measure the exact amount of pressure produced by the bandage splint. A specific application for which the inflatable bandage splint will have beneficial application is the use over a skin graft after surgery upon the hand. If the inflatable bandage splint is made of transparent materials, the graft can be continuously inspected during the healing process. Still further the inflatable bandage splint can be used to apply gentle pressure to the hand to control blood oozing. Where the bandage splint is provided with more than one valve through the outer envelope, the bandage splint can be used to heat or cool a hand by circulating either cold or hot fluids through the inflatable compartment of the bandage splint.

It is necessary according to this invention that the inner glove and the outer envelope be connected in some way, otherwise no restraint of the hand takes place until the inner glove touches the outer glove. A feature of this invention is the selection of the locations where the inner glove the outer envelope are connected to provide for the proper protection of the hand when the bandage splint is inflated.

Where both sides of the glove and envelope have approximate equal sizes, the bandage splint will tend to hold the hand in a palm-and-fingers-flat-on-the-table position which is not natural or comfortable. Any stretching of the outer envelope will result in greater tension at the stretched location. Thus, when the hand is bent after inflation, there will be greater tension in the portion of the outer envelope that is further stretched. The balance of forces will then tend to return the hand to the unbent position where all portions of the outer envelope are equally stretched. The unbent position, as explained above, is not the natural and comfortable position for the hand. It is a particular feature of this invention to provide an inflatable hand bandage splint which enables the retention of the hand in its natural or bent position.

Often after surgery, it is desirable to permit the hand to be flexed or bent in one direction but not another. For example, with surgery on the back of the hand, it might be desirable to restrain the bending of the fingers and hand inwardly toward the palm but permissible to allow the extension of the palm or fingers into a flat position. The inflatable hand bandage splint according to this invention can be adapted to provide that degree of restricted mobility.

BRIEF DESCRIPTION

Briefly according to this invention, an inflatable bandage splint is provided for immobilizing a human hand. The bandage splint comprises an inner glove shaped to generally conform to the human hand. It should be slightly larger than the hand upon which it is to be placed. Typically, the inner glove comprises an easily sterilized plastic or elastomeric material. Preferably the material is transparent. Preferably the glove is shaped so that it will be generally unstretched or not more stretched on one side than the other when the hand is in its natural cupped position. However, in this embodiment, it is necessary to provide different bandage splints for each of the right and left hands. An outer envelope of impermeable elastic sheet material is provided covering the inner glove. Basically the same material that is useful for the inner glove is useful for the outer envelope with the only practical difference being the materials for the outer envelope will have a greater sheet thickness. The inner glove and the outer envelope are sealed together to form a fluid-tight chamber surrounding the fingers, hands and wrists as the case may be. The fluid tight chamber may be inflated through a valve or valves provided in the outer envelope. The inner glove and outer envelope are secured together at selected distal locations, for example, at the fingertips and thumbtip and in the vicinity of the wrist. It may be desirable to provide inner connections between the inner glove and the outer envelope; for example, at the space between the bases of two fingers. If the connection between the inner glove and the outer envelope were not made at selected locations, then the hand within the inflated outer envelope would be free to move until it struck the outer envelope. Eyelets are provided secured to the outer envelope at at least some of the selected distal locations where the inner glove and outer envelope are connected. Eyelets are also provided at the proximal end of the bandage splint, say, about the wrist. In this way, pencil members may be threaded through the eyelets and tied to bias the hand in the inflated bandage splint in the desired curve position. By extending tensile members such as elastic strings from the tips of the fingers to the palm or side of the wrist, the hand can be drawn into a cup position. By extending tensile members from the tips of the fingers to the eyelets on the dorsal side of the wrist, the hand can be drawn into a more-or-less flat position. According to a preferred embodiment, the bandage splint has at least two separately inflatable compartments; one on the dorsal side of the hand and one on the palmar side of the hand. In this way, one or the other compartment may be filled with a settable fluid such as room temperature vulcanizing silicone and the other side may simply be inflated with air. Thus, the hand may be held by the bandage splint to provide for limited flexing in one direction only.

The above described inflatable hand bandage splint is light, soft and has no sharp edges and thus will not produce pressure sores. It can be adjusted easily to changes in swelling by deflating or inflating it further without removing it. By reducing swelling, the bandage splint will reduce pain. When it comes time to remove the inflatable hand bandage splint described above, it is easy to remove and replace and no mechanical instruments or forceful manipulations are required. Where the inner glove and outer envelope are made from transparent materials, the fingertips as well as the wounds or grafts can be easily observed. Complications such as hematoma or infection can be detected and easily treated.

Most important, inflatable gloves will allow positioning of the fingers and hand at the desired angle in relation to the wrist and the fingers at the desired angle with relation to the palm. This is accomplished by means of tensile members threaded through the eyelets and tied together. The inflatable hand bandage splint is lightweight and therefore allows free motion of the elbow and shoulder, preventing these joints from becoming stiff for lack of exercise. The inflatable hand bandage splint is especially useful for protecting the hands of children, and older patients who are in a coma or uncontrollable psychiatric patients, to protect them from hurting themselves or others, and to prevent them from removing or pulling their own dressings on other parts of the body.

THE DRAWINGS

Further features and other objects and advantages of this invention will become clear from the following detailed description made with reference to the drawings in which FIG. 1 is a dorsal or palmar view of one embodiment of a bandage splint according to this invention wherein the inner glove is surrounded by a mitten-shaped outer envelope, FIG. 2 is a dorsal or palmar view of an embodiment of this invention wherein the inner glove is surroundered by a glove-shaped outer envelope, FIG. 3 is a dorsal or palmar view of an embodiment according to this invention wherein the inner glove does not enclose the most distal phalanges, FIG. 4 is a dorsal or palmar view of an embodiment according to this invention wherein the inner glove and outer envelope define more than one separately inflatable compartment;

DESCRIPTION OF THE PREFERRED EMBODIMENTS

Figure 1:
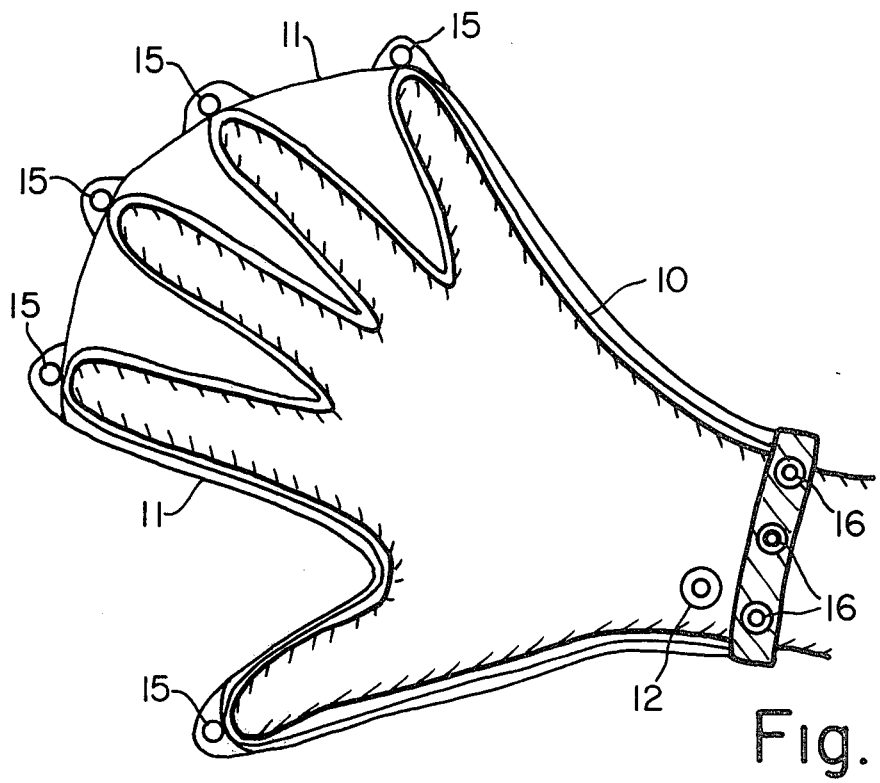
Figure 5:
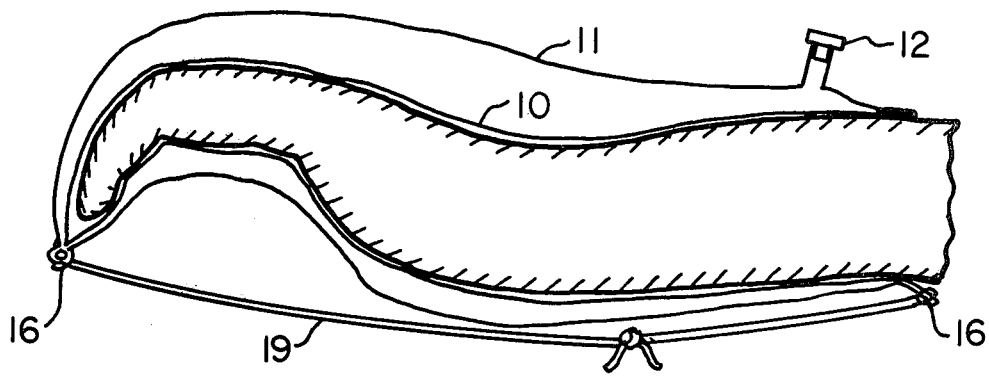
FIG. 5 is a section view of the embodiment according to FIG. 1 or 2.
Figure 6:
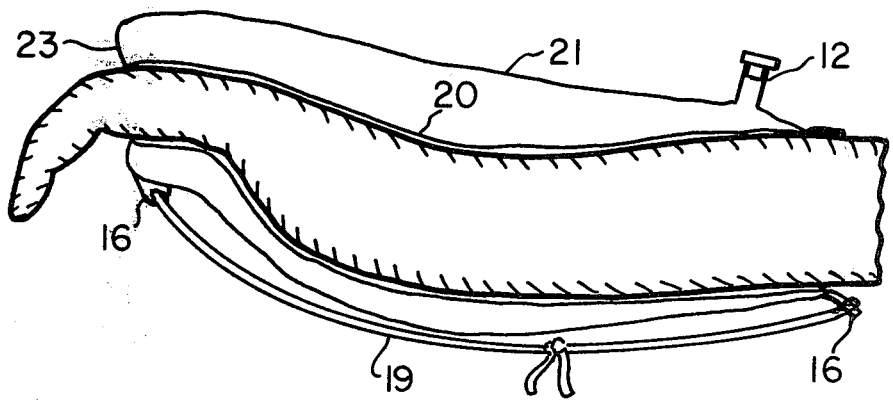
FIG. 6 is a section view of the embodiment according to FIG. 3.

Referring now to FIG. 1, there is shown a hand surrounded by an inflatable bandage splint according to this invention. An inner glove 10 is shown draped over the hand. The inner glove is constructed much like a regular hand glove. Preferably, it is sized to loosely fit over the hand; however, it may be sized such that some stretching is required to emplace the inner glove over the hand. Surrounding the inner glove is an outer envelope 11. Preferably both the inner glove and outer envelope are comprised of transparent materials. They must be comprised of fluid impermeable materials. Preferably, they are comprised of plastic or elastomeric materials. It is useful if the outer envelope is of sufficient thickness and elasticity such that the desired pressures and tensile forces can be achieved without excessive ballooning of the outer envelope. In some embodiments, the outer layer is sufficiently thick so that it does not stretch substantially when inflated. The outer envelope and the inner glove are sealed together to define at least one inflatable compartment. Thus, in FIG. 1, the inner glove is glove-shaped and the outer envelope is mitten-shaped and the two must be sealed together around the periphery of the proximal or wrist end of the glove. A valve and valve stem permits the compartment to be inflated through the outer envelope. The valve and valve stem are available products. Opening and closing the valve may be accomplished by twisting or sliding the valve in the stem. The inner glove and outer envelope must be connected together at selected distal locations. As shown in FIG. 1, the selected locations 15 are at the fingertips and at the thumbtip. As shown in FIG. 5, eyelets may be provided at the fingertips and in the vicinity of the wrist secured to the outer envelope. Tensile members such as elastic strings or rubber bands may be threaded through the eyelets and tied to draw the hand into the desired flexion position when it is necessary for example after certain surgical operations. The valve is shown at the proximal (wrist) end of the inflatable hand bandage splint. Inflation can be accomplished either with a hand bulb which accompanies a typical blood pressure measuring apparatus or by mouth. A second valve and valve stem may be provided if the inflatable glove is used for circulating either hot or cold fluids through the space between the inner glove and outer envelope to warm or cool the hand. The splint can be used to massage the hand. By attaching it to a small alternating motor pump, it will inflate and deflate at set intervals and will produce a massaging effect that helps reduce swelling and improve circulation.

Figure 2:
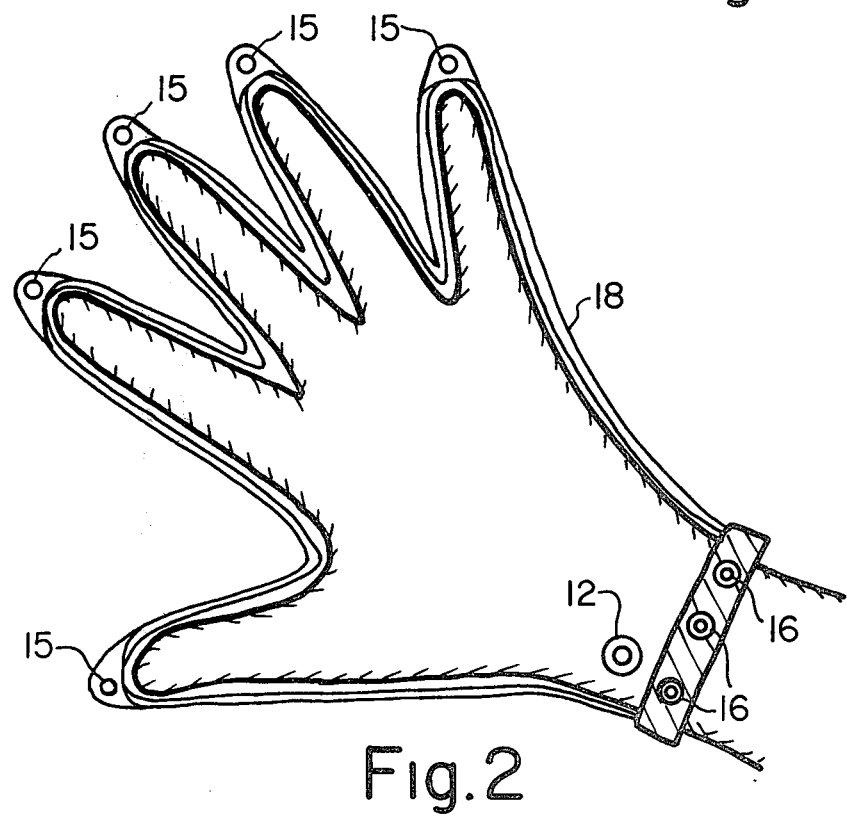

Referring now to FIG. 2, there is shown an alternate embodiment of this invention in which the outer envelope 18 is glove-shaped. All the other elements corresponding to those found in FIG. 1 have alike numerals.

Figure 3:
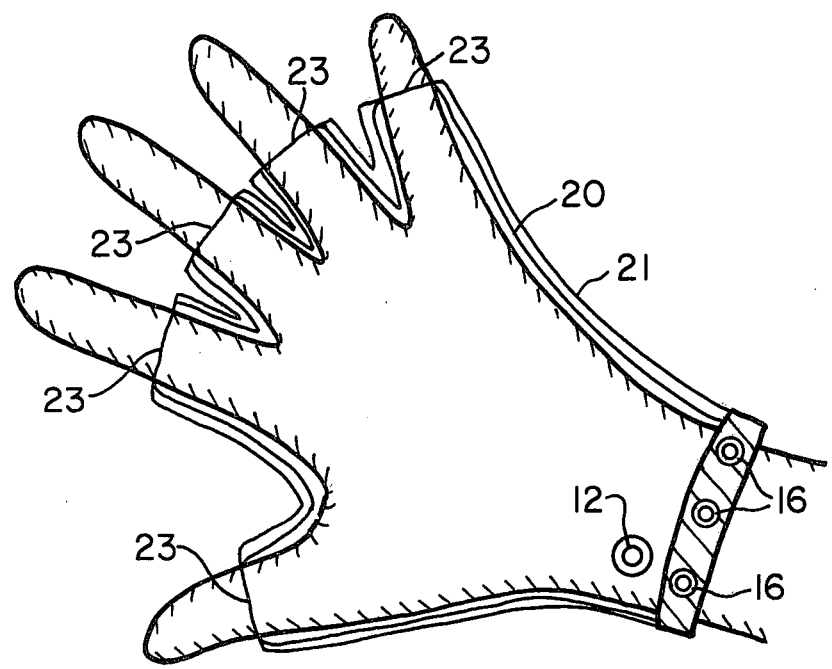

Referring now to FIG. 3, there is shown yet another embodiment of this invention in which the inner glove 20 and outer envelope 21 comprise partial gloves with the distal ends of the phalanges exposed. The embodiment illustrated in FIG. 3, to the extent that the elements thereof are identical with those shown in FIG. 1, carry the same identifying numerals. The distal connections 23 between the inner glove 20 and the outer envelope 21 occur at the location where the fingers of the glove terminate. With this embodiment, it is easy to observe the coloration and condition of swelling in the finger tips and the distal ends of the fingers are permitted a certain amount of mobility. The eyelets are provided at least on the palmar side of the fingers where the gloves 20 and 21 are joined. Thus the hand may be pulled into the desired flexion position even though the ends of the fingers are exposed. By threading a tensile member 19 through the eyelets and tying at the appropriate length.

Figure 4:
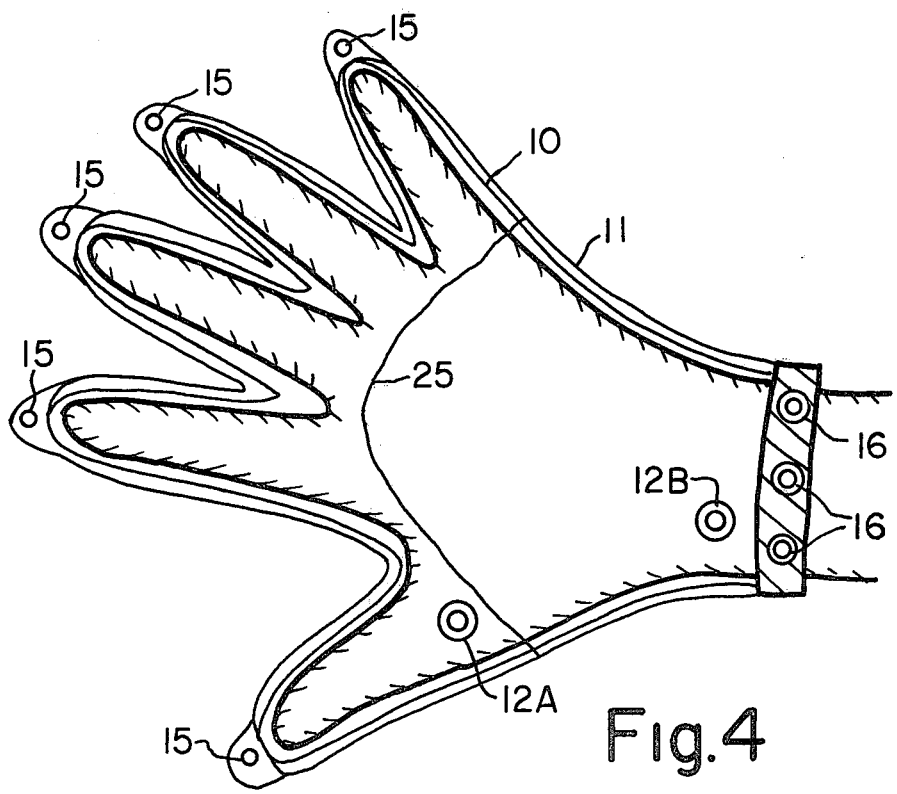

Referring to FIG. 4, there is shown an embodiment according to this invention in which one inflatable compartment is provided between the outer envelope and the inner glove. The compartments are defined by joining the inner glove and outer envelope along the compartment boundaries to construct a fluid impermeable seal along the boundary. Of course, an additional valve must be provided to enable the individual and separate inflation of both compartments. Such a boundary is illustrated by a line 25 on FIG. 4. Elements of the embodiment illustrated in FIG. 4 which are identical with those illustrated in FIG. 1 bear like numerals. Where the inflatable compartment or space between the inner glove and outer envelope are divided into individually inflatable compartments, it is at least desirable to provide a dorsal compartment over the back of the hand and a palmar compartment over the front of the hand. The backs of the fingers may be associated with the dorsal compartment and the front of the fingers with the palmar compartment. In yet a further preferred embodiment, the fingers are surrounded by yet a third compartment connected to neither the dorsal compartment nor the palmar compartment. In the latter embodiment, yet another valve is required.

Having thus defined my invention with the particularity required by the Patent Laws, what is desired protected by Letters Patent is set forth in the following claims.

I claim:

1. An inflatable bandage splint for immobilizing the human hand comprising:
   an inner glove shaped to generally conform to the human hand,
   an outer elastic envelope just larger than the said inner glove,
   means for sealing the glove and envelope together at the proximal ends thereof,
   means for securing the glove and enclosure together at selected distal locations, and
   a plurality of eyelets associated with the outer envelope at at least some of the selected distal locations, and a plurality of eyelets at the proximal end of the inflatable bandage splint whereby tensile members may be strung through the eyelets and tied to provide the desired neutral position of the hand when the bandage splint is inflated.

2. An inflatable bandage splint according to claim 1 wherein the outer envelope is also glove-shaped.

3. An inflatable bandage splint according to claim 1 wherein the outer envelope is mitten-shaped.

4. An inflatable bandage splint according to claim 1 wherein the selected distal locations are the tips of each finger and thumb.

5. An inflatable bandage splint according to claim 2 wherein eyelets are provided at each selected distal location where the inner glove and outer envelope are joined.

6. An inflatable bandage splint according to claim 3 wherein a plurality of eyelets are spaced about the proximal end and with at least one eyelet on the palmar side and one eyelet on the dorsal side of the outer envelope.

7. An inflatable bandage splint according to claim 1 wherein the inner glove is a partial glove leaving exposed at least portions of the fingers and thumb.

8. An inflatable bandage splint according to claim 7 wherein the glove is a partial glove leaving exposed at least a portion of the most distal phalanges of the four fingers.

9. An inflatable bandage splint according to claim 1 wherein the glove extends in the proximal direction to surround at least a portion of the radius and the ulna bones in the forearm.

10. An inflatable bandage splint according to claim 1 wherein the inner glove is fabricated of fluid impermeable material and the outer envelope is fabricated of elastic fluid impermeable material.

11. An inflatable bandage splint according to claim 1 wherein the outer envelope has two valves therein such that fluid may be circulated therethrough.

12. An inflatable bandage splint according to claim 1 wherein the bandage splint has at least two separately inflatable compartments one on the dorsal side and one on the palmar side of the hand.

13. An inflatable bandage splint according to claim 12 wherein the bandage splint has at least three separately inflatable compartments including one surrounding the fingers, one on the dorsal side of the hand, and one on the palmar side of the hand.

14. An inflatable bandage splint according to claim 1 wherein each face of the glove and the outer envelope are identical such that the glove can be used on either the right or left-hand.

15. An inflatable bandage splint according to claim 1 wherein the dorsal side of the glove and envelope are somewhat larger than the palmar sides thereof such that upon inflation the hand will be held in a naturally flexed position.

16. A method of immobilizing the human hand for limited flexing comprising
   (a) placing the hand in a bandage splint comprising an inner glove and an outer envelope with joins therebetween to define a plurality of chambers about the hand with individual valves into each chamber
   (b) filling at least one chamber with a settable filler and
   (c) inflating at least one of the remaining chambers with a compressible fluid.

* * * * *